(12) United States Patent
Back et al.

(10) Patent No.: US 10,716,710 B2
(45) Date of Patent: Jul. 21, 2020

(54) METHOD FOR MANUFACTURING A SEALING RING, AND A SEALING RING

(71) Applicant: WIKMANSHYTTAN SAFETY AB, Vikmanshyttan (SE)

(72) Inventors: Arne Back, Johanneshov (SE); Martin Bonnevier, Jarfalla (SE); Per Moller, Leksand (SE)

(73) Assignee: WIKMANSHYTTAN SAFETY AB, Vikmanshyttan (SE)

( * ) Notice: Subject to any disclaimer, the term of this patent is extended or adjusted under 35 U.S.C. 154(b) by 404 days.

(21) Appl. No.: 15/741,799

(22) PCT Filed: Jul. 6, 2015

(86) PCT No.: PCT/SE2015/050793
§ 371 (c)(1),
(2) Date: Jan. 4, 2018

(87) PCT Pub. No.: WO2017/007379
PCT Pub. Date: Jan. 12, 2017

(65) Prior Publication Data
US 2018/0193199 A1   Jul. 12, 2018

(51) Int. Cl.
*A61F 11/14*   (2006.01)
*H04R 1/10*   (2006.01)
(Continued)

(52) U.S. Cl.
CPC .............. *A61F 11/14* (2013.01); *A42B 3/166* (2013.01); *B29C 45/006* (2013.01); *B29C 65/58* (2013.01);
(Continued)

(58) Field of Classification Search
CPC ....... A61F 11/14; A42B 3/166; B29C 45/006; B29C 65/58; B29C 66/727; G10K 11/16; H04R 1/1008
See application file for complete search history.

(56) References Cited

U.S. PATENT DOCUMENTS 3,645,354 A * 2/1972 Kliewer ............... H04R 1/1008
                                                          181/129
4,572,323 A * 2/1986 Randall .................... A61F 11/14
                                                          181/129
(Continued)

FOREIGN PATENT DOCUMENTS

DE   8302827 U1   6/1983
WO   9015584 A1   12/1990
(Continued)

OTHER PUBLICATIONS

European search report dated Apr. 23, 2019, from corresponding European Patent Application No. 15897833.8-1210.
(Continued)

*Primary Examiner* — Forrest M Phillips
(74) *Attorney, Agent, or Firm* — Young & Thompson

(57) ABSTRACT

Disclosed is a method for manufacturing a generally circular, oval or rectangular sealing ring for an acoustic device, the sealing ring being configured for being in contact with the skin of a user during use. The method includes: forming, in an injection molding step, a covering being generally U-shaped in cross-section; and attaching the end sections of the covering to a support element. The invention also relates to a sealing ring of the above-mentioned type.

20 Claims, 12 Drawing Sheets

(51) Int. Cl.

| | | |
|---|---|---|
| *A42B 3/16* | (2006.01) | |
| *B29C 45/00* | (2006.01) | |
| *B29C 65/58* | (2006.01) | |
| *B29C 65/00* | (2006.01) | |
| *G10K 11/16* | (2006.01) | |
| *B29C 45/14* | (2006.01) | |
| *B29L 31/26* | (2006.01) | |

(52) U.S. Cl.
CPC ............ *B29C 66/727* (2013.01); *G10K 11/16* (2013.01); *H04R 1/1008* (2013.01); *B29C 45/14* (2013.01); *B29L 2031/26* (2013.01); *H04R 1/1083* (2013.01)

(56) References Cited

U.S. PATENT DOCUMENTS

| | | | | |
|---|---|---|---|---|
| 4,830,138 A * | 5/1989 | Palmaer | ............... | A61F 11/14 181/129 |
| 5,920,911 A * | 7/1999 | Cushman | ............... | A61F 11/14 181/129 |
| 5,970,160 A * | 10/1999 | Nilsson | ............... | H04R 1/1083 381/371 |
| 7,036,157 B1 * | 5/2006 | Andersson | ............... | A61F 11/14 181/129 |
| 7,717,226 B2 * | 5/2010 | Purcell | ............... | A61F 11/14 181/129 |
| 8,944,061 B2 * | 2/2015 | D'Souza | ............... | A61M 16/0816 128/206.24 |
| 2003/0044038 A1 | 3/2003 | Shirata | | |
| 2008/0128198 A1 * | 6/2008 | Du | ............... | A61F 11/14 181/129 |

FOREIGN PATENT DOCUMENTS

| | | |
|---|---|---|
| WO | 9519750 A1 | 7/1995 |
| WO | 9748296 A1 | 12/1997 |
| WO | 0103623 A1 | 1/2001 |
| WO | 02060365 A1 | 8/2002 |

OTHER PUBLICATIONS

International Search Report, dated Mar. 23, 2016, from corresponding PCT/SE2015/050793 application.

* cited by examiner

US 10,716,710 B2

METHOD FOR MANUFACTURING A SEALING RING, AND A SEALING RING

TECHNICAL FIELD

The invention relates to a method for manufacturing a generally circular, oval or rectangular sealing ring for an acoustic device, said sealing ring being configured to rest against the head of a user during use.

The invention also relates to a sealing ring for an acoustic device and having a generally circular, oval or rectangular form and being configured to rest against the head of a user during use.

The invention can be used in connection with hearing protection devices or alternatively audio headphones and similar devices.

BACKGROUND

In many fields of industry and in many types of workplaces, it is common to use hearing protection devices due to excessive levels of noise and sound in the environment. Such a hearing protection device can for example be in the form of a pair of cup-shaped elements which are connected by means of a connecting element, i.e. a headband or a helmet, wherein each cup-shaped element comprises a generally circular or oval sealing ring which is configured to cover an ear of the user. During use, the sealing ring is intended to rest against the head of a user, thereby enclosing the ear. In this way, the sealing ring defines a sealing and makes it comfortable for the user to wear the hearing protective device by distributing the pressure acting upon the user's head through the sealing ring. More precisely, the sealing ring can be designed generally as a cushion, having a covering surface foil which encloses a foam material.

Optionally, the cup-shaped element can be provided with noise-attenuating material, for example foam material which is designed to absorb sound. Also, the cup-shaped element with the sealing ring can be used so as to form a set of headphones or audio ear muffs. There are different kinds of audio ear muffs, e.g. with built-in radio, communication facilities or active volume technology. In such cases, the cup-shaped element accommodates a loudspeaker.

With regard to a hearing protection device of the above-mentioned type, it is important to design it with a high degree of sound attenuation and also with a high degree of comfort so as to allow a user to wear it for long periods of time. It is also important that the hearing protection is durable and is resistant against wear and degradation due to influence from the environment. It can be noted that the above-mentioned sealing ring is an important component in order to achieve these objects. It is particularly important that a hearing protection device of the above-mentioned type, including the sealing ring, can be manufactured in a simple and cost-effective manner.

Hearing protection devices of the above-mentioned type are previously known. As an example, the patent document U.S. Pat. No. 5,970,160 discloses a hearing protection device comprising a sealing ring with a foam material and a shell element.

Furthermore, the patent document WO 97/48296 discloses a hearing protection device which comprises a sealing ring which is manufactured from a foam material, for example polyurethane. The sealing ring is mounted onto a shell element.

In order to provide an efficient manufacturing process of a hearing protection device of the known type, it is also previously known to manufacture the shell from a generally stiff plastic material such as ABS (acrylonitrile butadiene styrene). Furthermore, the hearing protection device can generally be manufactured in accordance with a process involving injection molding of a support element in the form of a generally annular and plate-shaped component which is made for example from PVC or ABS material. Furthermore, a soft cushion having a surface foil made from PVC and enclosing a foam material is used for manufacturing a sealing ring which is configured as a sealing which is in contact with the user during use. This sealing ring is attached to the plate-shaped component by means of, for example, a suitable adhesive material or by means of welding. Finally, the support element is attached to the shell element. In this manner, a complete hearing protection device is manufactured.

A disadvantage with today's technology for manufacturing a sealing ring for hearing protection devices is that it comprises a high number of manufacturing steps and that it is unnecessarily complex, time-consuming and expensive. Furthermore, such sealing rings are manufactured from materials having a negative impact on the environment. Another aspect concerning the use and storage of hearing protector devices with sealing rings made of PVC is the relatively poor temperature resistance. Too high temperatures can result in deformation, affecting the sealing and attenuating properties.

Consequently, there is a continuing need for improved ways of manufacturing such a sealing ring, in order to improve the efficiency of the manufacturing process and to lower the manufacturing costs.

SUMMARY

Consequently, an object of the invention is to provide a method for manufacturing a sealing ring which solves the above-mentioned problems related to prior art and provides a solution which is more cost-efficient than previously known methods.

The above-mentioned object is achieved by a method for manufacturing a generally circular, oval or rectangular sealing ring for an acoustic device, said sealing ring being configured to rest against the head of a user during use. The method comprises the step of: forming, in an injection molding step, a covering being generally U-shaped in cross-section; and attaching the end sections of said covering to a support element.

The invention provides certain advantages over previously known technology, primarily due to the fact that it relates to a process involving one or more injection molding steps which define a simple and cost-efficient manufacturing process. The method according to the invention also leads to advantages in the form of an improved and highly accurate control over dimensions and over the design of the acoustic device.

The invention can be used in an acoustic device such as a hearing protection device, or alternatively in other forms of acoustic devices such as headphones.

A further object of the invention is to provide a sealing ring which solves the above-mentioned problems related to prior art and provides a solution which has advantages related to environment-friendliness, temperature resistance and sound-attenuation as compared with previously known sealing rings.

This object is obtained by means of a sealing ring for an acoustic device and having a generally circular, oval or rectangular form and being configured to rest against the head of a user during use. The sealing ring comprises a covering being generally U-shaped in cross-section and being formed by injection molding; and a support element, the end sections of which are attached to a support element.

Further advantages and advantageous features of the invention are disclosed in the following description and in the dependent claims.

BRIEF DESCRIPTION OF THE DRAWINGS

With reference to the appended drawings, below follows a more detailed description of embodiments of the invention cited as examples.

DESCRIPTION OF EMBODIMENTS

Different embodiments of the present disclosure will be described more fully hereinafter with reference to the accompanying drawings. The method and devices disclosed herein can, however, be realized in many different forms and should not be construed as being limited to the embodiments described below.

Also, the terminology used herein is for the purpose of describing particular aspects of the disclosure only, and is not intended to limit the disclosure. As used herein, the singular forms "a", "an" and "the" are intended to include the plural forms as well, unless the context clearly indicates otherwise.

Figure 1:
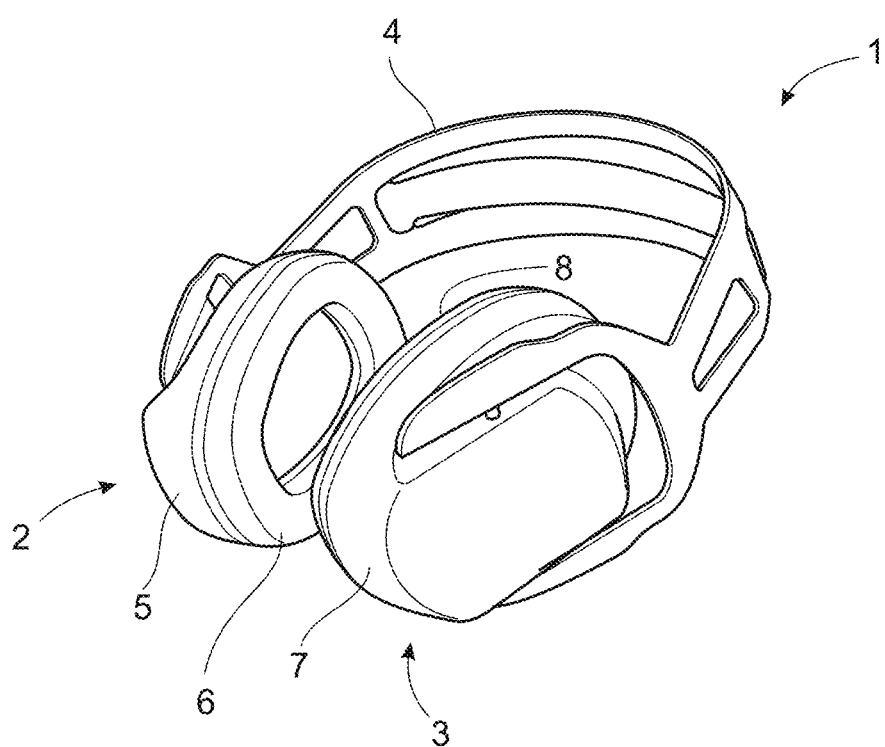
FIG. 1 shows a first embodiment of the invention in the form of a hearing protection device.

With initial reference to FIG. 1, there is shown a schematical perspective view of an acoustic device in the form of a hearing protection device 1 being formed of two generally similar ear units 2, 3 which are connected by means of a headband 4. The headband 4 is suitably of a flexible but relatively stiff and flexible material which is configured so that the ear units 2, 3 are positioned in a defined position upon each ear of a user during use.

The first ear unit 2 comprises a first ear cup 5 to which a first sealing ring 6 is attached. In a corresponding way, the second ear unit 3 comprises a second ear cup 7 to which a second sealing ring 8 is attached. In the following, only the first ear cup 5 will be described. It should however be noted that both ear cups 5, 7 are of similar construction. Also, the sealing rings 6, 8 are generally formed as two oval cushions, wherein each one may or may not comprise flexible foam material, as will be described in more detail below. Although FIG. 1 shows sealing rings 6, 8 which are oval-shaped, it should be noted that they could alternatively be designed in circular or rectangular form, or virtually any form which defines an aperture allowing the sealing rings to be positioned around the ears of a user.

The invention is described herein in connection with an embodiment in which it is used in a hearing protection device. It should be noted, however, that the principles of the invention can alternatively be used in other forms of acoustic devices, such as active hearing protection devices and also headphones.

According to an embodiment of the invention, the ear cups 5, 7 are formed as a stiff shell from a suitable plastic material, for example ABS (acrylonitrile butadiene styrene) or another suitable material.

Optionally, the ear cups 5, 7 cups may contain sound-attenuating material such as foam material, in order to optimize the sound-damping properties of the complete hearing protection device 1. There exist different kinds of audio ear muffs, e.g. with built-in radio, communication facilities and active volume technology. Such devices are not described in greater detail here.

Also, although the term "shell" is used to describe the first ear cup 5, it could alternatively be designed as any type of shell, cup, bowl or container which is configured for supporting the first sealing ring 6 and for allowing the headband 4 to be attached.

Figure 2:
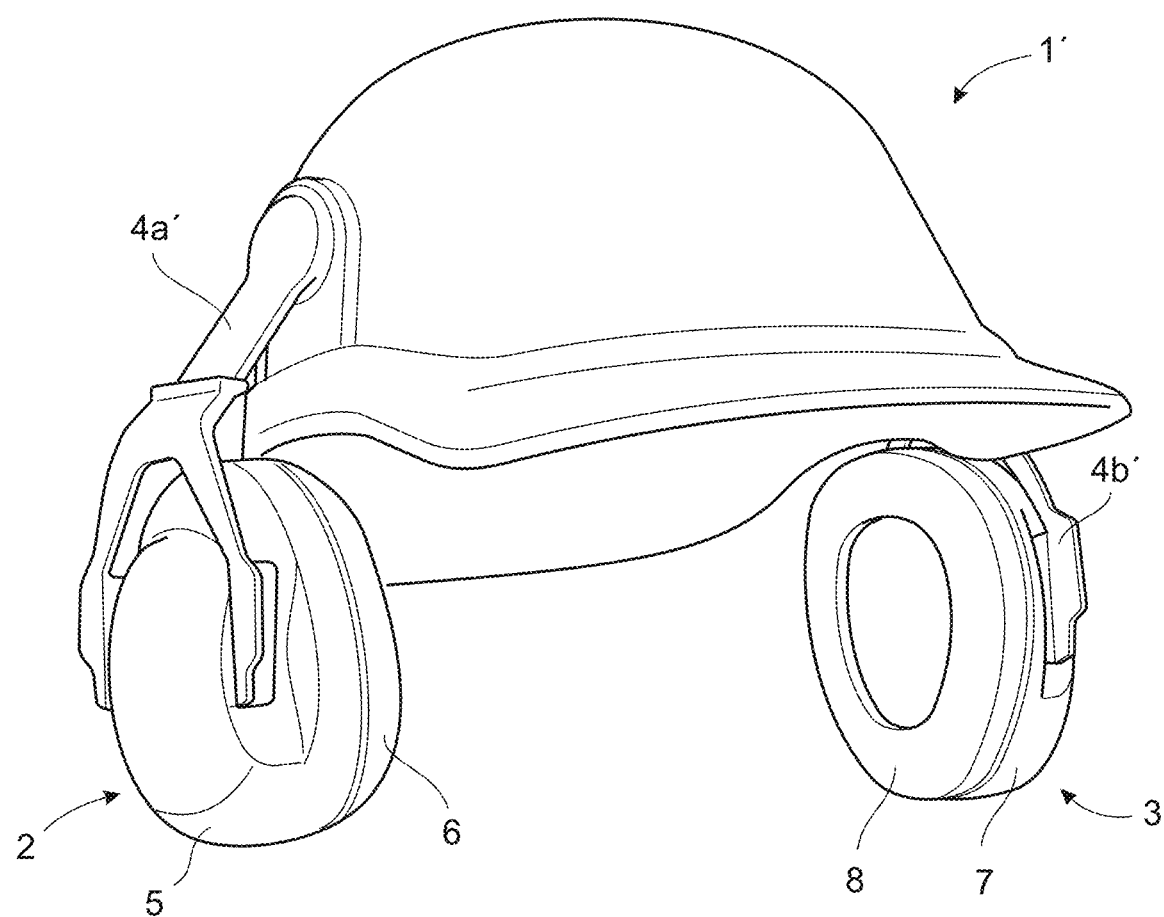
FIG. 2 shows an alternative hearing protection device.

Also, the invention can be used in connection with hearing protection devices attached to a helmet. FIG. 2 shows an embodiment involving such a modified hearing protection device 1'. As shown in FIG. 2, each one of two ear units 2, 3—which are both of the same construction as described with reference to FIG. 1—are provided with a modified headband 4a" and 4b", respectively. The embodiment shown in FIG. 2 is used together with a helmet but is otherwise functionally equivalent to the embodiment shown in FIG. 1.

The first sealing ring 6 is attached to the first ear cup 5 in a manner which is not apparent from FIG. 1 or FIG. 2 but will now be described below with reference to FIG. 3, which is a cross-sectional view through the first sealing ring 6 as described above, and with reference to FIG. 4, which is a perspective view of a cut-away section of the sealing ring 6.

Figure 3:
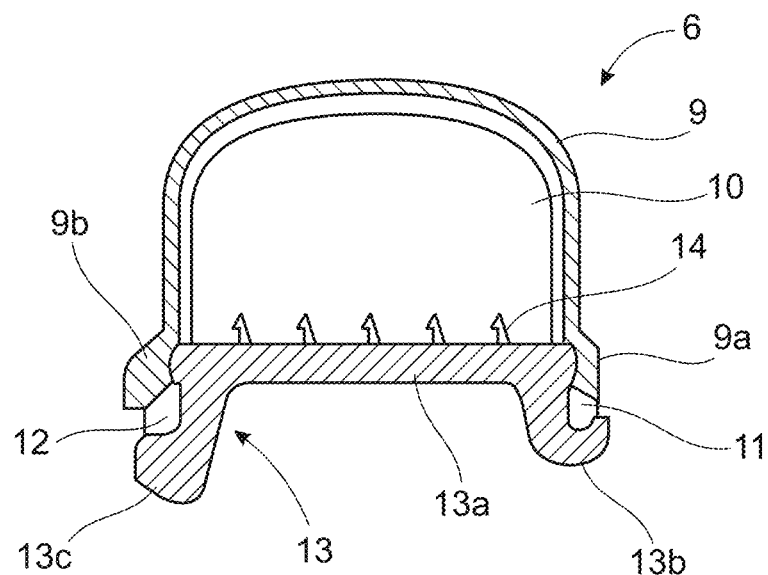
FIG. 3 shows a sealing ring in accordance with a first embodiment of the invention.
Figure 4:
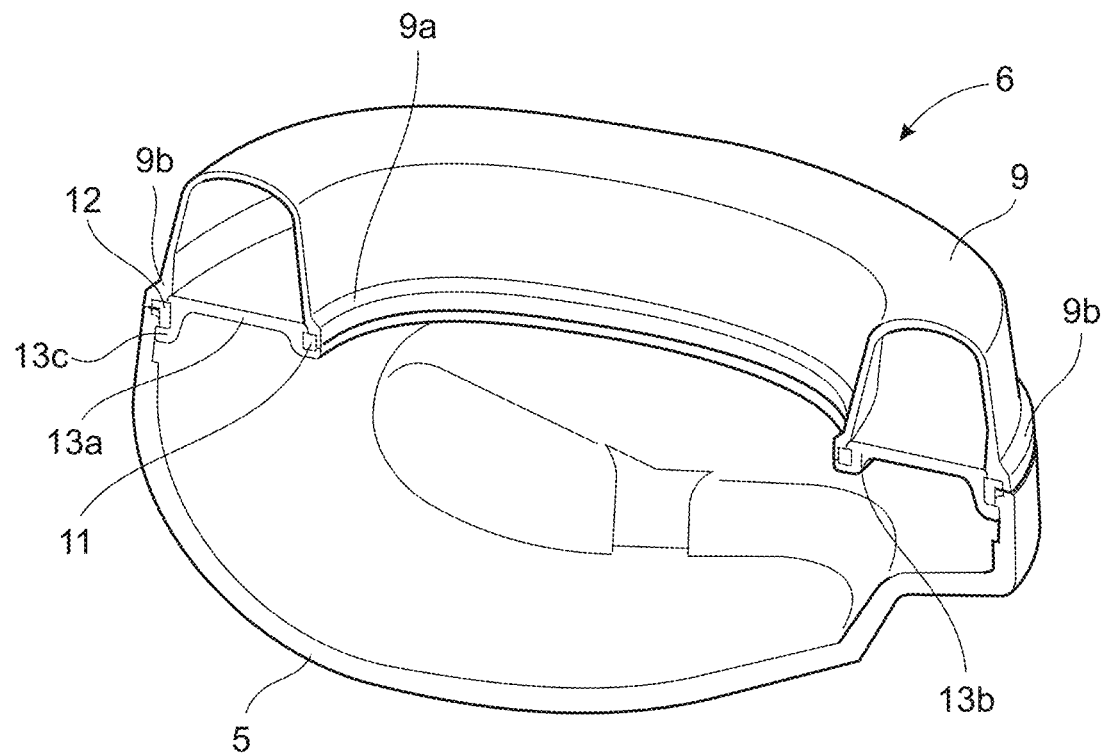
FIG. 4 shows a cut-away perspective view of a sealing ring according to an embodiment.

As shown in FIG. 3, the first sealing ring 6 comprises a generally annular and U-shaped (as seen in cross-section) covering 9 which according to an embodiment is formed by an injection moldable material, suitably TPS, which is a material of the TPE (thermoplastic elastomer) type, and which forms a soft covering which during use rests against the head of a user, i.e. around an ear of the user. The invention is not limited to TPE material but can be implemented with generally any form of material which is injection moldable.

According to the embodiment shown in FIG. 3, the first sealing ring 6 accommodates an annular foam element 10 which is enclosed inside the covering 9 and forms an inner material with sound-attenuating and vibration-damping properties. The foam element 10 is preferably manufactured from polyurethane foam or another material with similar properties.

It should be noted that the invention is not limited to embodiments which comprise an annular foam element, but can in principle be implemented without any enclosed foam element. This will be described in greater detail below with reference to FIG. 7.

Furthermore, the covering 9 is formed with two annular, i.e. ring-shaped, or oval, protrusions 9a and 9b. Since the covering 9 forms a closed loop (which according to the embodiments shown in the drawings is oval), the first protrusion 9a defines an inner perimeter of the covering 9, whereas the second protrusion 9b defines an outer perimeter of the covering 9.

These two protrusions 9a, 9b are attached to two loop-shaped elements 11, 12 which can be of circular, oval or rectangular form, or any other form in which they form a closed loop and in which they also follow the form of the sealing ring 6 as a whole. According to the embodiment shown in the drawings, the loop-shaped elements 11, 12 are in the form of two ovals, of which the first loop-shaped element 11 has a smaller circumference than the second loop-shaped element 12.

In the following, the term "oval elements" will be used for describing said loop-shaped elements according to the embodiment. With reference for example to FIG. 3, it can be noted that the oval elements 11, 12 both extend around the perimeter of the sealing ring 6, the first oval element 11 being arranged around the inside of the sealing ring 6 and the second oval element 12 being arranged along the outside of the sealing ring 6. The two oval elements 11, 12 are suitably formed by a relatively stiff material such as PP (polypropylene), ABS or PA (polyamide).

Furthermore, the two protrusions 9a, 9b and the two oval elements 11, 12 are formed so as to co-operate with a generally annular support element 13 which extends along generally the same periphery as the sealing ring 6. The support element 13 is suitably made from ABS plastic or another material with similar properties.

The protrusions 9a, 9b and the two oval elements 11, 12 are designed in a manner so that an annular part 13a of the support element 13 can be snap-fitted into the oval elements 11, 12 in order to form the complete sealing ring 6. In particular, the support element 13 has an upper annular portion 13a which, along its inner periphery and outer periphery, has a projecting portion which co-operates with a similarly shaped but inwardly extending recess along the inside of the protrusions 9a, 9b. Also, the lower part of the support element 13 has an extending section 13c which is intended to be secured to the cup element 5, 7 (not shown in FIG. 3).

According to an embodiment, the upper side of the support element 13 is proved with a plurality of hook-shaped elements 14 having the purpose of holding the foam element 10 in place on the support element 13. As an alternative to these hook-shaped elements 14, the support element 13 can be provided with other forms of fastening means, such as a suitable adhesive or similar.

Consequently, during manufacturing of the sealing ring 6, the support element 13 is snap-fitted into the two oval elements 11, 12 as indicated in FIG. 3, while the foam element 10 is held in place by means of the hook-shaped elements 14 during assembly.

A method of manufacturing the sealing ring 6 will now be described with reference to FIG. 5, which is a flow chart of the manufacturing process. Initially, it should be noted that a first injection molding tool or tool part is used during this manufacturing process. The first injection molding tool (or tool part) is formed with a recess or cavity, the internal shape of which corresponds to the final shape of the above-mentioned covering 9. According to the embodiment, the cross-section of the recess is generally U-shaped. Furthermore, a second injection molding tool (or tool part) which is configured with recesses for the two above-mentioned oval elements 11, 12 is also used. The two injection molding tools (or tool parts) are moveable in relation to each other.

Figure 5:
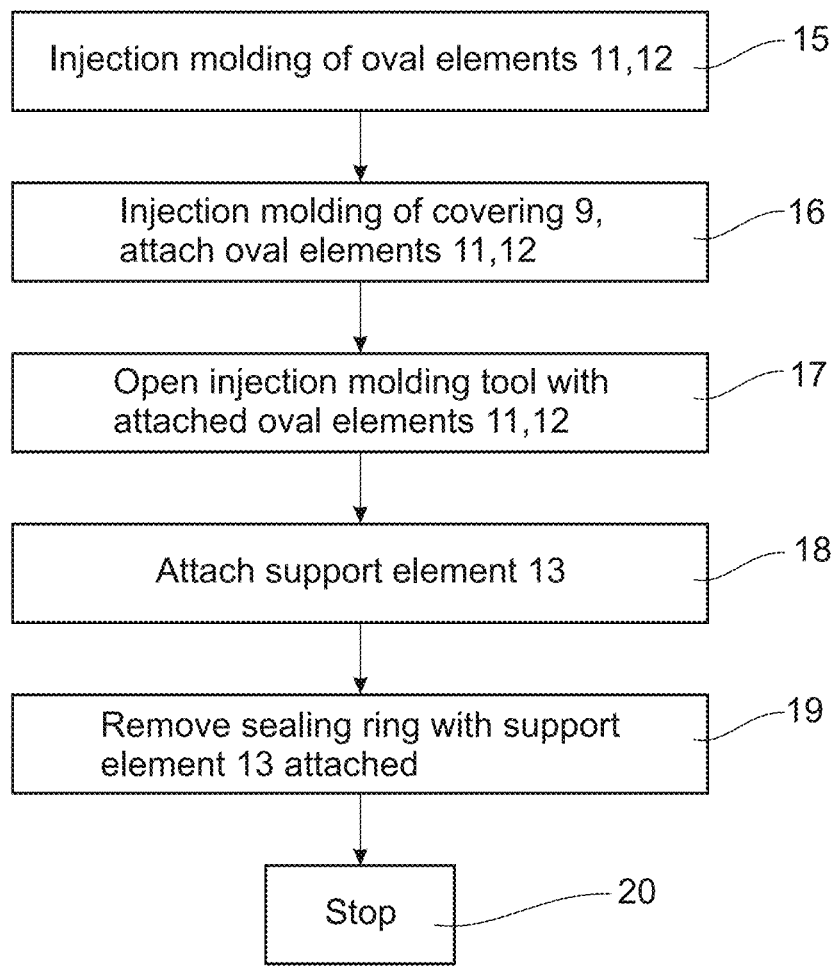
FIG. 5 shows a flow chart which discloses a method for manufacturing an acoustic device according to an embodiment of the invention.

The first stage in the manufacturing process, as indicated by means of step 15 in FIG. 5, is that the two oval elements 11, 12 are injection molded in the second injection molding tool. Next, the second injection molding tool with the two molded oval elements 11, 12 is moved to a position in front of the aperture of the first injection molding tool. In this manner, the covering 9 is injection molded in a manner so that the two oval elements 11, 12 are attached to the covering 9 (see step 16 in FIG. 5).

Next, the first injection molding tool is opened so that the covering 9 remains in the injection molding tool with the oval elements 11, 12 attached thereto (step 17). The next step is that the support element 13—on which the foam element 10 has been previously mounted—is locked by snap-fitting in the oval elements 11, 12 and the lower, protruding parts 9a, 9b of the covering 9 (step 18).

The description above with reference to FIG. 5 relates to an injection molding process using two separate tools, or tool parts. However, the invention can also be implemented with the use of one single tool being designed to accommodate cavities for the above-mentioned components.

It should be noted that the snap-fitting, i.e. the locking, of the support element 13 is made possible through a suitable design of the inner and outer periphery of the support element 13 and the periphery of each oval element 11, 12.

Finally, the entire sealing ring 6 is removed from the first injection molding tool in a manner wherein the support element 13 remains fixed, i.e. attached to the oval elements 11, 12 and the lower part of the covering 9 (step 19). Finally, the manufacturing process is terminated (step 20).

In this manner, a simple and cost-effective process for manufacturing the sealing ring 6 is provided, which comprises one or more simple injection molding steps. This is an important advantage of the invention.

Figure 6:
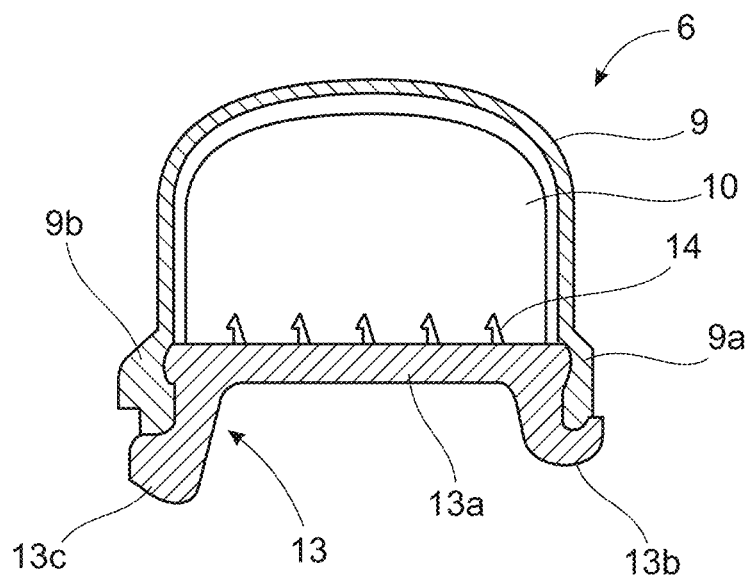
FIG. 6 shows a sealing ring in accordance with a second embodiment of the invention.

FIG. 6 shows an alternative embodiment of the invention, in which the oval elements 11, 12 mentioned above are omitted. Instead, the covering 9 is shaped with two lower protrusions 9a, 9b which are designed in a manner so as to directly interact with the support element 13. In other words, the covering 9 is injection molded with the two protrusions 9a, 9b, which are formed—as shown in FIG. 6—with internal recesses which cooperate with outwardly protruding sections in the inner and outer periphery of the annular portion 13a of the support element 13. In this manner, the support element 13 can be attached directly to the covering 9 without any oval elements as shown in the embodiment in FIG. 3.

Figure 7:
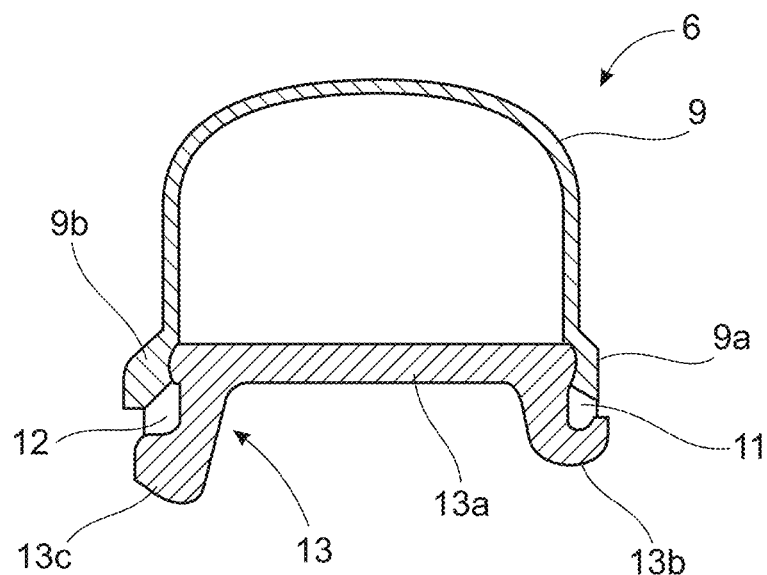
FIG. 7 shows a sealing ring in accordance with a third embodiment of the invention.

Furthermore, FIG. 7 discloses an embodiment of the invention which is similar to the embodiment in FIG. 3 but in which no foam element is used. As a consequence, no hook-shaped elements are used in the support element 13. This embodiment is based on the concept that the covering 9 itself is sufficient for providing the necessary sealing and sound-attenuating properties for the sealing ring 6.

Figure 8:
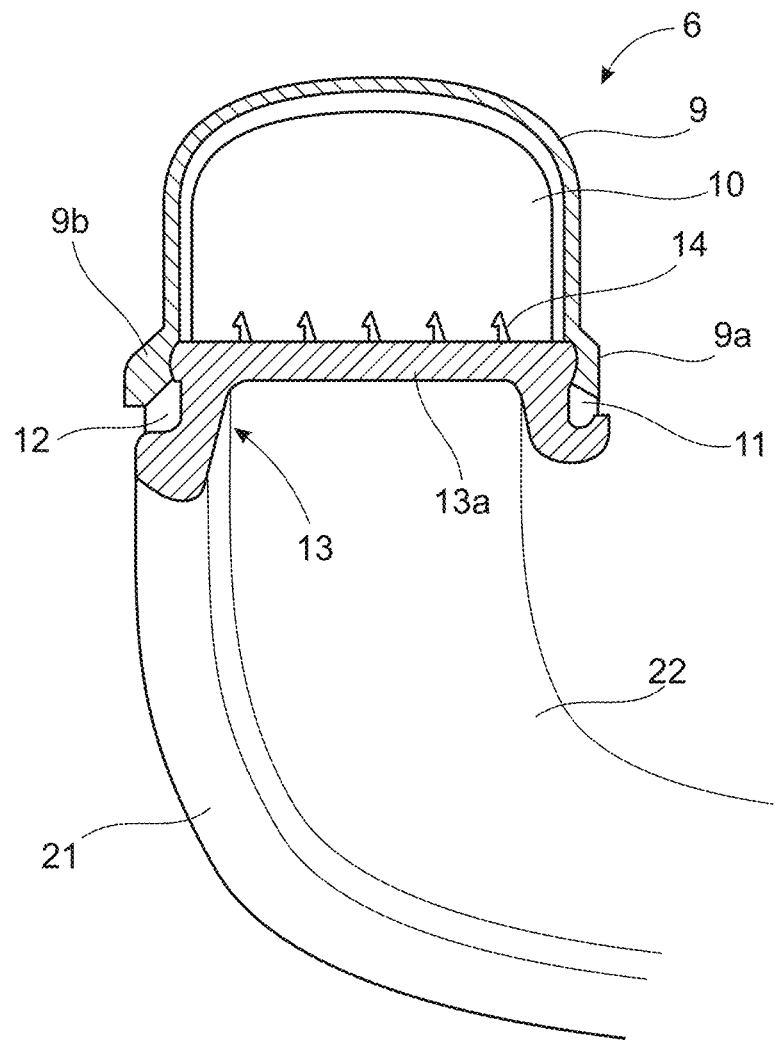
FIG. 8 shows a sealing ring in accordance with a fourth embodiment of the invention.

FIG. 8 shows a further embodiment in which the support element is not constituted by a separate element which in turn is attached to an ear cup. Instead, the support element 13 as shown in FIG. 8 forms an end section of an ear cup wall 21, i.e. the support element 13 is here integrated with the structure of the ear cup wall 21. Inside the ear cup wall 21, a sound-attenuating material 22 is arranged. Also, as explained with reference to the embodiment of FIG. 3, for example, the support element 13 is provided with a plate-shaped element 13a which carries a number of hook-shaped elements 14 for fastening a foam element 10.

Figure 9:
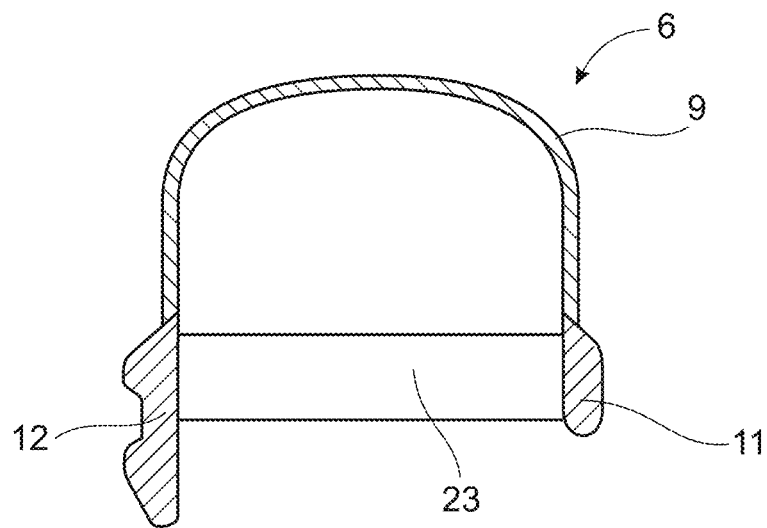
FIG. 9 shows a sealing ring in accordance with a fifth embodiment of the invention.
Figure 10:
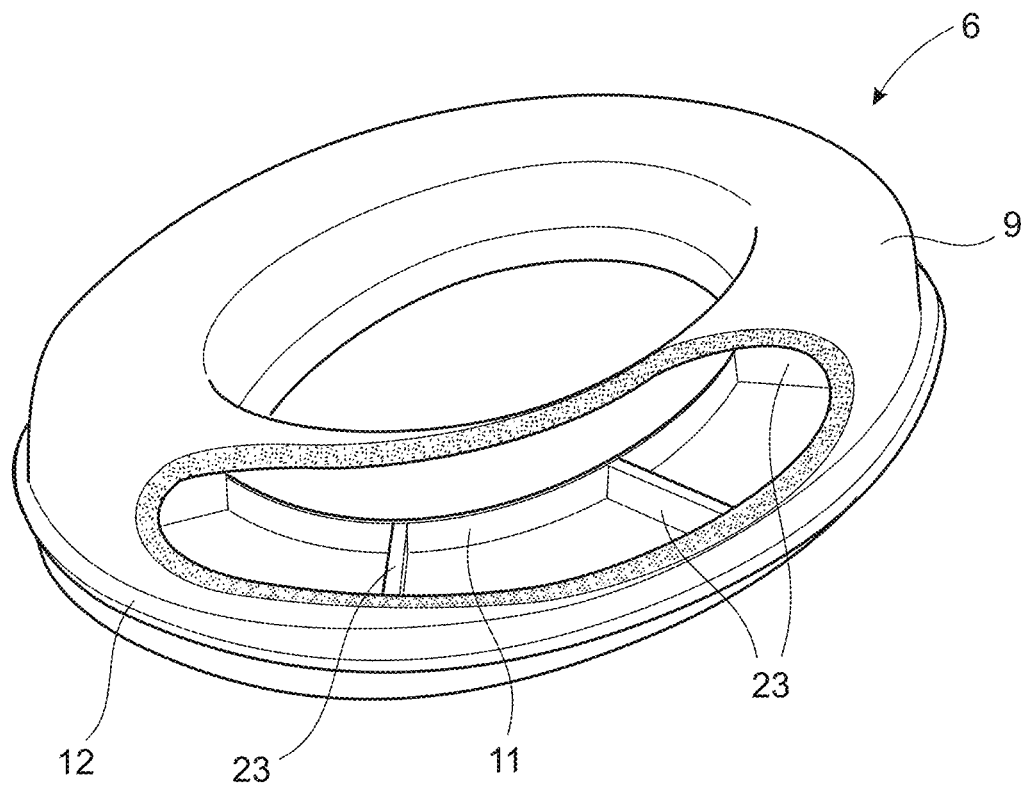
FIG. 10 is a partly cut-away perspective view of the fifth embodiment.

FIGS. 9 and 10 show a further embodiment in which the support element 13 as described above is omitted. Also, the embodiment shown in FIGS. 9 and 10 is based on the use of two oval elements 11, 12 which are connected by means of a number of spokes 23 extending in a generally transversal manner between the oval elements 11, 12. This embodiment is based on a manufacturing process in which the two oval elements 11, 12 are connected with the spokes 23. After this, the covering 9 is injection molded and attached to the oval elements 11, 12. According to this embodiment, no support element of the type which is mentioned above is used. Also, there is no need for any foam element inside if the covering 9 obtains the necessary properties of the sealing ring 6.

Figure 11:
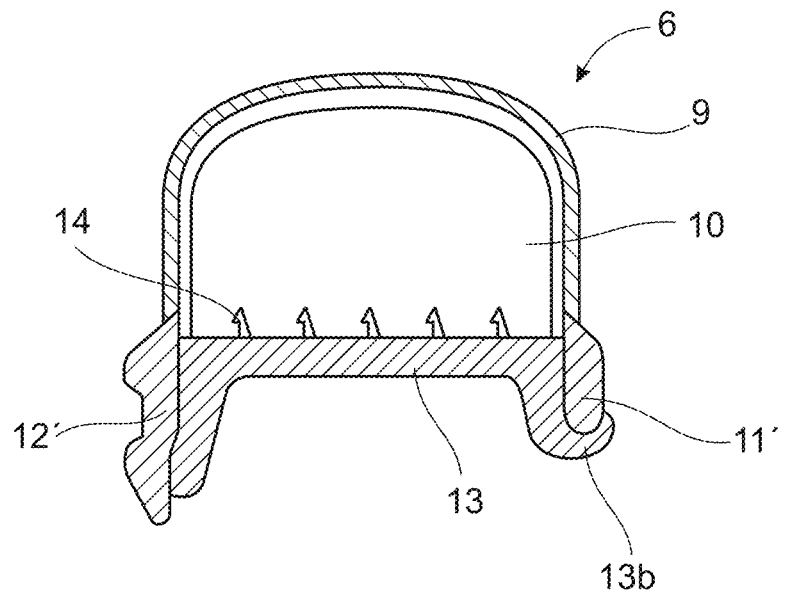
FIG. 11 shows the sealing ring according to FIG. 10 but in a perspective view.

FIG. 11 shows a further embodiment of the invention which comprises a covering 9 and a foam element 10 as described above. This embodiment also comprises an alternative first loop-shaped element 12' extending around the outside of the sealing ring 6. This loop-shaped element 12' is configured to be attached to the cup element 5, 7 (as shown in FIGS. 1 and 2). Furthermore, this embodiment comprises a second alternative loop-shaped element 11' which extends along the inside of the sealing ring 6. Also, the support element 13 as shown in FIG. 11 is arranged to be attached to the inside of the first loop-shaped element 12'.

Figure 12:
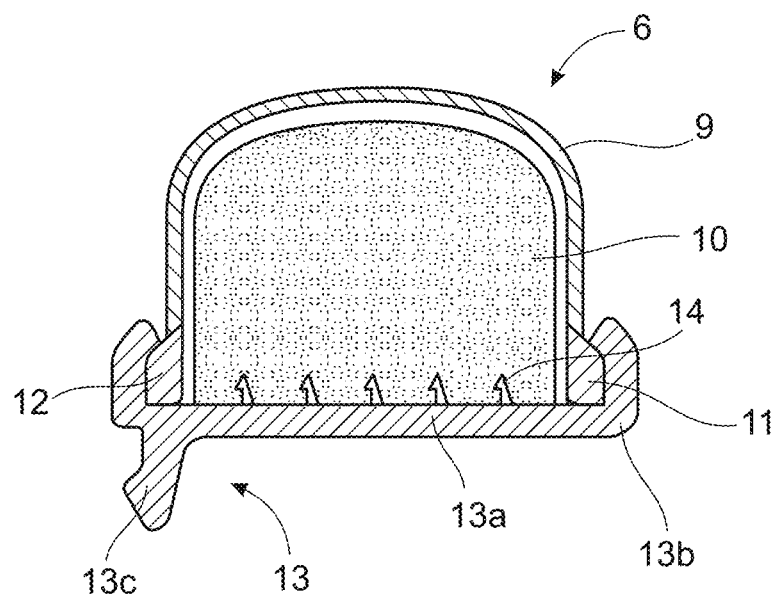
FIG. 12 shows a sealing ring in accordance with a sixth embodiment of the invention.

FIG. 12 shows a further embodiment of the invention, which comprises a support element 13 which is modified as compared with, for example, the support element shown in FIG. 3. More precisely, the support element 13 in FIG. 12 is configured for a snap-in fastening on the upper side of the two loop-shaped elements 11, 12. This is obtained by forming the support element 13 with two upwardly projecting elements which extend over each loop-shaped element 11, 12 so as to snap in as shown in FIG. 12. The support element 13 also has a lower element 13c which is intended to be attached to an ear cup 5, 7.

According to a further embodiment, which is not shown in the drawings, the sealing ring 6 is provided with one or more air channels connecting the interior of the covering 9 with the outside. The purpose of such an air channel is to reduce vibrations in the sealing ring 6. According to said embodiment, such an air channel is defined by forming a suitable surface where the support element 13 is in contact with one of the oval rings 11, 12 with a groove or duct which connects the air volume inside the covering 9 with the exterior.

It is to be understood that the present invention is not limited to the embodiments described above and illustrated in the drawings; rather, the skilled person will recognize that many changes and modifications may be made within the scope of the appended claims.

The invention claimed is:

1. A method for manufacturing a generally circular, oval or rectangular sealing ring (6) for an acoustic device (1; 1"), said sealing ring (6) being configured to rest against the head of a user during use;
   said method comprising:
   forming, in an injection molding step (16), a covering (9) being generally U-shaped in cross-section;
   forming, in a further injection molding step (15), two generally loop-shaped elements (11, 12) of which one element (11) has less circumference than the other element (12);
   connecting said loop-shaped elements (11; 12) to said covering (9); and
   attaching (18) the end sections (9a, 9b) of said covering (9) to a support element (13), thereby attaching said support element (13) between said loop-shaped elements (11, 12).

2. Method according to claim 1, wherein said method comprises:
   attaching a foam element (10) which extends inside said covering (9).

3. Method according to claim 1, wherein said method comprises:
   attaching said support element (13) by snap-fitting into said loop-shaped elements (11, 12).

4. Method according to claim 1, wherein said method comprises:
   forming an air connection between the interior of said covering and the outside of said covering.

5. Sealing ring (6) for an acoustic device (1; 1') and having a generally circular, oval or rectangular form and being configured to rest against the head of a user during use;
   wherein said sealing ring (6) comprises:
   a covering (9) being generally U-shaped in cross-section and being formed by injection molding;
   a support element (13), the end sections (9a, 9b) of which are attached to a support element (13); and
   two generally loop-shaped elements (11, 12) of which one element (11) has less circumference than the other element (12), said elements (11, 12) being formed by injection molding and said support element (13) being attached between said loop-shaped elements (11, 12).

6. Sealing ring (6) according to claim 5, wherein:
   said loop-shaped elements (11, 12) are designed with a generally circular, oval or rectangular form.

7. Sealing ring (6) according to claim 5, wherein:
   the support element (13) holds a foam element (10) configured to be enclosed by said covering (9).

8. Hearing protection device (1; 1') comprising a sealing ring (6) according to claim 5.

9. Audio headphone set comprising a sealing ring according to claim 5.

10. Method according to claim 2, wherein said method comprises:
    attaching said support element (13) by snap-fitting into said loop-shaped elements (11, 12).

11. Method according to claim 2, wherein said method comprises:
    forming an air connection between the interior of said covering and the outside of said covering.

12. Method according to claim 3, wherein said method comprises:
    forming an air connection between the interior of said covering and the outside of said covering.

13. Method according to claim 10, wherein said method comprises:
    forming an air connection between the interior of said covering and the outside of said covering.

14. Sealing ring (6) according to claim 6, wherein:
    the support element (13) holds a foam element (10) configured to be enclosed by said covering (9).

15. Hearing protection device (1; 1') comprising a sealing ring (6) according to claim 6.

16. Hearing protection device (1; 1') comprising a sealing ring (6) according to claim 7.

17. Hearing protection device (1; 1') comprising a sealing ring (6) according to claim 14.

18. Audio headphone set comprising a sealing ring according to claim 6.

19. Audio headphone set comprising a sealing ring according to claim 7.

20. Audio headphone set comprising a sealing ring according to claim 14.

\* \* \* \* \*